US007498025B1

(12) United States Patent
Briesewitz et al.

(10) Patent No.: US 7,498,025 B1
(45) Date of Patent: *Mar. 3, 2009

(54) TARGETED BIFUNCTIONAL MOLECULES AND THERAPIES BASED THEREON

(75) Inventors: Roger Briesewitz, Mountain View, CA (US); Gerald R. Crabtree, Woodside, CA (US); Thomas J. Wandless, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 144 days.

This patent is subject to a terminal disclaimer.

(21) Appl. No.: 09/716,842

(22) Filed: Nov. 17, 2000

Related U.S. Application Data

(60) Provisional application No. 60/166,580, filed on Nov. 19, 1999.

(51) Int. Cl.
*A61K 38/00* (2006.01)
*C07K 7/06* (2006.01)
*C07K 5/10* (2006.01)
*C07K 5/00* (2006.01)
*C12N 9/90* (2006.01)

(52) U.S. Cl. .................. 424/94.5; 424/94.1; 424/193.1; 424/194.1; 514/2; 514/9; 514/11

(58) Field of Classification Search .............. 424/193.1, 424/194.1, 195.11, 198.1; 530/391.1, 391.3, 530/39, 3
See application file for complete search history.

(56) References Cited

U.S. PATENT DOCUMENTS

| 5,382,657 | A | 1/1995 | Karasiewicz et al. |
| 5,620,708 | A | 4/1997 | Amkraut et al. |
| 5,718,915 | A | 2/1998 | Virtanen et al. |
| 5,830,462 | A | 11/1998 | Crabtree et al. |
| 5,834,266 | A | 11/1998 | Crabtree et al. |
| 5,840,733 | A | 11/1998 | Krantz et al. |
| 5,843,440 | A | 12/1998 | Pouletty et al. |
| 5,869,337 | A | 2/1999 | Crabtree et al. |
| 5,871,753 | A | 2/1999 | Crabtree et al. |
| 5,965,106 | A | 10/1999 | Pomato et al. |
| 6,066,319 | A | 5/2000 | Halperin et al. |
| 6,372,712 | B1 * | 4/2002 | Briesewitz et al. .............. 514/2 |
| 6,670,348 | B1 | 12/2003 | Rosen et al. |
| 6,921,531 | B2 * | 7/2005 | Briesewitz et al. ......... 424/94.5 |
| 2002/0045570 | A1 | 4/2002 | Rosen et al. |

FOREIGN PATENT DOCUMENTS

| WO | WO 91/01743 | 2/1991 |
| WO | WO 94/18317 | 8/1994 |
| WO | WO 95/02684 | 1/1995 |
| WO | WO 95/05389 | 2/1995 |
| WO | WO 95/10302 | 4/1995 |
| WO | WO 96/06111 | 2/1996 |
| WO | WO 96/12796 | 5/1996 |
| WO | WO 96/13613 | 5/1996 |
| WO | WO 97/25074 | 7/1997 |
| WO | WO 97/29372 | 8/1997 |
| WO | WO 98/00171 | 1/1998 |
| WO | WO 98/11437 | 3/1998 |
| WO | WO 98/46270 | 10/1998 |
| WO | WO 98/47002 | 10/1998 |
| WO | WO 98/47916 | 10/1998 |
| WO | WO 99/61055 | 12/1999 |
| WO | WO 01/35748 | 5/2001 |
| WO | WO 01/36612 | 5/2001 |

OTHER PUBLICATIONS

Pichon et al, Mole Pharmacology 51(3): 431-38; 1997.*
Briesewitz et al, Proc Natl. Acad Sci USA 96: 1953-58, Mar. 1998.*
Stryer et al, in Biochemistry, Third edition, W H Freeman Company, New York, pp. 31-33, 1998.*
Ngo et al, 1994, The Protein Folding Problem and Tertiary Structure Prediction, pp. 492-495.*
Szepeshazi et al, Anticancer Drugs 8(10): 974-87, Nov. 1997.*
Nagy et al, Proc Natl Acad Sci USA 93: 2464-2469, Mar. 1996.*
Nagy et al, Proc Natl Acad Sci USA 93: 7269-7273, Jul. 1996.*
Forsgren et al, Cancer Res 39(12): 5155-64, Dec. 1979.*
Asai et al, Acta Endocrinol (Copenh) 87(1): 173-80, Jan. 1978.*
Trouet et al, Proc Natl Acad Sci USA 79: 626-629, Jan. 1982.*
Rihova et al, Advanced Drug Delivery Reviews 29: 273-289, 1998.*
Al-Obeidi, et al., (1990) "Synthesis and Actions of a Melanotropin Conjugate, Ac-[Nle$^4$, Glu(gamma-4'-hydroxyanilide)$^5$, D-Phe$^7$]α-MSH$_{4-10}$-NH$_2$, on Melanocytes and Melanoma Cells In Vitro," *Journal of Pharmaceutical Sciences* vol. 79, No. (6):500-504.
Atwell, John L., et al., (1996) "Design and Expression of a Stable Bispecific scFv Dimer With Affinity for Both Glycophorin and N9 Neuraminidase," *Molecular Immunology* vol. 22, No. (17/18):1301-1312.
Belshaw, et al., (1996) "Controlling Protein Association and Subcellular Localization with a Synthetic Ligand that Induces Heterodimerization of Proteins," *Proc. Natl. Acad. Sci. U.S.A.* vol. 93 4604-4607.
Bernstein, Kenneth E., et al., (1990) "A Deeply Recessed Active Site in Angiotensin-Converting Enzyme Is Indicated From the Binding Characteristics of Biotin-Spacer-Inhibitor Reagents," *Biochemical and Biophysical Communications* vol. 167, No. (1):310-316.

(Continued)

*Primary Examiner*—Phuong Huynh
(74) *Attorney, Agent, or Firm*—Bozicevic, Field & Francis LLP; Bret E. Field

(57) ABSTRACT

Targeted bifunctional molecules and methods for their use are provided. The subject targeted bifunctional molecules are conjugates of a drug moiety and a targeting moiety, where these two moieties are optionally joined by a linking group. The bifunctional molecules are further characterized in that they exhibit a modulated biodistribution upon administration to a host as compared to a free drug control. The subject targeted bifunctional molecules find use in a variety of therapeutic applications.

29 Claims, No Drawings

OTHER PUBLICATIONS

Bourdouxhe-Housiaux, Catherine, et al., (1996) "Interaction of DNA-Threading Peptide-Amsacrine Conjugates With DNA and Chromatin," *Anti-Cancer Drug Design* vol. 11:509-525.

Brochu, et al., (1992) "Modes of Action and Inhibitory Activities of New Siderophore-β-Lactam Conjugates that use Specific Iron Uptake Pathways for Entry into Bacteria," *Antimicrobial Agents and Chemotherapy* vol. 36, No. (10):2166-2175.

Briesewitz, et al., (1999) "Affinity Modulation of Small-Moelcule Ligands by Borrowing Endogenous Protein Surfaces," *P.N.A.S* vol. 96, No. (5):1953-1958.

Chakraborty, TK., et al., (1995) "Design and Synthesis of a Rapamycin-Based High Affinity Binding FKBP12 Ligand," *Chemistry & Biology* vol. 2:157-161.

Crabtree, Gerald R., et al., (1996) "Three-Part Inventions: Intracellular Signalling and Induced Proximity," *Elsevier Trends Journal* pp. 418-422.

Heath, et al., (1986) "liposome-Mediated Delivery of Pteridine Antifolates to cells in Vitro: Potency of Methotrexate, and its α and γ Substituents," *Biochimica et Biophysica Acta* vol. 862:72-80.

Ho, Steffan N., et al., (1996) "Dimeric Ligands Define a Role for Transcriptional Activation Domains In Reinitation," *Nature*, vol. 382, No. (6594):822-826.

Holt, et al., (1994) "Structure-Activity Studies of Synthetic FKBP Ligands as Peptidyl-Prolyl Isomerase Inhibitors," *Bioorganic and Medicinal Chemistry Letters* vol. 4, No. (2):315-320.

Kramer, Werner, et al., (1992) "Liver-Specific Drug Targeting by Coupling to Bile Acids," *The Journal of Biological Chemistry*, vol. 267, No. (2):18598-18604.

Luengo, et al., (1994) "Synthesis and Structure-Activity Relationships of Macrocyclic FKBP Ligands," *Bioorganic and Medicinal Chemistry Letters* vol. 4, No. (2):321-324.

Lussow, et al., (1996) "Targeting of Antihapten Antibodies to Activated T Cells via an IL-2-Hapten Conjugate Prolongs Cardiac Graft Survival," *Transplantation* vol. 62, No. (12):1703-1708.

Maeda, et al., (1997) "Amino Acids and Peptides XXXII: A Biofunctional Poly(Ethylene Glycol) Hybrid of Fibronectin-Related Peptides,"*Biochemical and Biophysical Research Communications* vol. 241:595-598.

Mogre, R.M., et al., (1987) "A New Carbene Based Heterbifunctional Reagent: Photochemical Crosslinking of Aldolase," *FEBS Letters*, vol. 221., No. (2):408-414.

Mu, Yu., et al., (1987) "Bioconjugation of Laminin Peptide YIGSR With Poly(Styrene Co-Maleic Acid) Increases Its Antimetastatic Effect on Lung Metastatis of B16-BL6 Melanoma Cells," *Biochemical and Biophysical Research Communications*, vol. 255:75-79.

Varshavsky, Alexander, (1998) "Codominant Interference, Antieffectors, and Multitarget Drugs," *Proc. Natl. Acad. Sci. USA*, vol. 95:2094-2099.

Varshavsky, Alexander, (1995) "Codominance and Toxins: A Path to Drugs of Neatly Unlimited Selectivity," *Proc. Natl. Acad. Sci. USA*, vol. 92:3663-3667.

Zunino, et al., (1984) "Compassion of Antitumor Effects of Daunorubicin Covalently Linked to Poly-L-Amino Acid Carriers," *Eur. J. Cancer Chem. Oncol.* vol. 20, No. (3):421-425.

Choi et al. (1996) "Structure of the FKBP12-Rapamycin Complex Interacting with the Binding Domain of Human FRAP." *Science*, vol. 273:239-242.

Clardy (1999) "Borrowing to make ends meet." *Proc. Natl. Acad. Sci. USA*, vol. 96:1826-1827.

Garboczi et al. (1996) "Structure of the complex between human T-cell receptor, viral peptide and HLA-A2." *Nature*, vol. 384:134-141.

Griffith et al. (1995) "X-Ray Structure of Calcineurin Inhibited by the Immunophilin-Immunosuppressant FKBP12-FK506 Complex." *Cell*, vol. 82:507-522.

Johnson et al. (1997) "Amino-terminal dimerization of an erythropoieitin mimetic peptide results in increased erythropoietic activity." *Chemistry & Biology*, vol. 4:939-950.

Kissenger et al (1995) "Crystal structures of human calcineurin and the human FKBP12-FK506-calcineurin complex." *Nature*, vol. 378:641-644.

Klemm et al. (1997) "Rapid targeting of nuclear proteins to the cytoplasm" *Current Biology*, vol 7:638-644.

Livnah et al. (1996) "Functional Mimicry of a Protein Hormone by a Peptide Agonist: The EPO Receptor Complex at 2.8Å" *Science*, vol. 273;464-471.

Riviera et al. (1996) "A humanized system for pharmacologic control of gene expression." *Nature Medicine*. vol. 2(9):1028-1032.

Spencer et al. (1993) "Controlling Signal Trasduction with Synthetic Ligands." *Science*, vol. 262:1019-1024.

Spencer et al. (1996) "Functional analysis of Fas signaling in vivo using synthetic inducers of dimerization." *Current Biology*, vol. 6(7):839-847.

Kuduk et al. "Synthesis and Evaluation of Geldanamycin-Testosterone Hybrids" *Bioorg. Med. Chem. Lett. 10* (2000) 1303-1306.

Whitney, Marsha et al. "Selective Control of Myoblast Proliferation by A Synthetic Ligand," (2000) Abstracts from American Heart Association Scientific Sessions, vol. 102(18): II.139.

* cited by examiner

TARGETED BIFUNCTIONAL MOLECULES AND THERAPIES BASED THEREON

CROSS REFERENCE TO RELATED APPLICATIONS

Pursuant to 35 U.S.C. §119 (e), this application claims priority to the filing date of the U.S. Provisional Patent Application Ser. No. 60/166,580 filed November 19, 1999, the disclosure of which is herein incorporated by reference.

This invention was made with United States Government support under Grant No. CA39612 awarded by National Institutes of Health. The United States Government has certain rights in this invention.

INTRODUCTION

1. Technical Field

The field of this invention is pharmacology.

2. Background of the Invention

Any chemical agent that affects any process of living is a drug. Drugs are a critical tool for health care practitioners as they are used in the prevention, diagnosis and treatment of disease. Because of their criticality to the health care profession, annual world investment into the research and development of new chemical agents with therapeutic potential reaches into the billions of dollars. As a result, a large number of drugs have been developed to date and new chemical agents having potential therapeutic utility are frequently discovered. Chemical agents that find, or have found, use as drugs include naturally occurring and synthetic small molecules, as well as larger molecules, such as proteinaceous compounds.

The safety and efficacy of a drug is determined by how well it effects its target in the disease tissue as compared to other locations of the host to which it is administered. Often the effects of a drug on its target in disease unrelated tissues causes serious side effects, e.g. systemic toxicity. For example, many drugs used to treat cancer are anti-proliferatives that effect not only cancer cells but all dividing cells. This untargeted activity leads to serious side effects because cells of the intestinal lining and blood forming cells are suppressed in the course of the treatment with such drugs. Similarly, many anti-infective agents cause side effects because they are directed against metabolic pathways in microbial pathogens that are present in human cells as well. In order to reduce the side-effects of drugs, a method to direct them to the desired location would be very helpful. Furthermore, the efficacy of a drug could be enhanced if the drug is selectively accumulated at the target location.

As such, of great interest to the pharmaceutical industry and related fields would be the development of a method for targeting small molecule drugs, where methods of targeting small molecule drugs which resulted in at least one of enhanced efficacy or reduced toxicity would be of particular interest.

Relevant Literature

Patent publications of interest include: WO 91/01743; WO 94/18317; WO 95/02684: WO 95/10302: WO 96/06111: WO 96/12796: WO 96/13613; WO 97/25074; WO 97/29372: WO 98/11437: WO 98/47916: U.S. Pat. No. 5,830,462: U.S. Pat. No. 5,843,440; and U.S. Pat. No. 5,871,753. References of interest include: Briesewitz et al. Proc. Nat'l Acad. Sci. USA (March 1999) 96: 1953-1958: Clardy, Proc. Nat'l Acad. Sci. USA (March 1999) 1826-1827: Crabtree & Schreiber, Elsevier Trends Journal (November 1996) 418-422: Spencer et al., Curr. Biol. (July 1996) 6:839-847: Spencer et al., Science (1993) 262: 1019: Chakraborty et al., Chem. & Biol. (March 1995) 2:157-161; Ho et al. Nature (1996) 382: 822: Riviera et al., Nature Medicine (1996) 2: 1028; Klemm et al., Current Biology (1997) 7: 638: Belshaw et al., Proc. Nat'l. Acad. Sci. USA (1996) 93: 4604: Livnah et al., Science (1996) 273: 464; Johnson et al. Chemistry and Biology, (1997) 4: 939: Garboczi et al., Nature (1996) 384:134: Kissenger et al., Nature (1995) 378:641: Griffith et al., Cell (1995) 82: 507; Choi et al. Science (1996) 273:239. Also of interest are Kramer et al., J. Biol. Chem. (1992) 267:18598-18604: and Varshavsky. Proc. Nat'l Acad. Sci. USA (March 1998) 95: 2094-2099: Varshavsky, Proc. Nat'l Acad. Sci. USA (April 1995) 92:3663-3667: and Mu et al., Biochem. Biophys. Res. Comm. (1999)255:75-79.

SUMMARY OF THE INVENTION

Targeted bifunctional molecules and methods for their use are provided. The subject targeted bifunctional molecules are conjugates of a drug moiety and a targeting moiety, where these two moieties are optionally joined by a linking group. The subject bifunctional molecules are further characterized in that they exhibit a modulated biodistribution upon administration to a host as compared to a free drug control. The subject targeted bifunctional molecules find use in a variety of therapeutic applications.

DEFINITIONS

The term "bifunctional molecule" refers to a non-naturally occurring molecule that includes a targeting moiety and a drug moiety, where these two components may be covalently bonded to each other either directly or through a linking group.

The term "drug" refers to any active agent that affects any biological process. Active agents which are considered drugs for purposes of this application are agents that exhibit a pharmacological activity. Examples of drugs include active agents that are used in the prevention, diagnosis, alleviation, treatment or cure of a disease condition.

By "pharmacologic activity" is meant an activity that modulates or alters a biological process so as to result in a phenotypic change, e.g. cell death, cell proliferation etc.

A "biodistribution modulating protein" is a protein to which the targeting moiety of the subject bifunctional molecule binds and that serves to recruit the bifunctional molecule to a particular biological location or compartment of a host. e.g. to the intracellular space, extracellular space, cell type, tissue type, subcellular location, and the like.

The term "biodistribution" refers to the tissue and cellular distribution profile of an agent upon administration to a host, i.e., how the agent is distributed among the various different tissues and cells of the host.

The term "efficacy" refers to the effectiveness of a particular active agent for its intended purpose, i.e. the ability of a given active agent to cause its desired pharmacologic effect.

DESCRIPTION OF THE SPECIFIC EMBODIMENTS

Targeted bifunctional molecules and methods for their use are provided. The to subject targeted bifunctional molecules are conjugates of a drug moiety and a targeting moiety, where these two moieties are optionally joined by a linking group. The bifunctional molecules are further characterized in that they exhibit a modulated biodistribution upon administration to a host as compared to a free drug control. The subject targeted bifunctional molecules find use in a variety of therapeutic applications.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Targeted Bifunctional Molecule

The targeted bifunctional molecule of the subject invention is a non-naturally occurring or synthetic compound that is a conjugate of a drug or derivative thereof and a targeting moiety, where these two moieties are optionally joined by a linking group. The targeted bifunctional molecule is further characterized in that the targeting and drug moieties are different, such that the bifunctional molecule may be viewed as a heterodimeric compound produced by the joining of two different moieties. In many embodiments, the targeting moiety and the drug moiety are chosen such that the corresponding drug target and binding partner of the targeting moiety, e.g. corresponding biodistribution modulating protein to which the targeting moiety binds, do not naturally associate with each other to produce a biological effect. As indicated above, the subject targeted bifunctional molecules are small. As such, the molecular weight of the targeted to bifunctional molecule is generally at least about 100 D, usually at least about 400 D and more usually at least about 500 D, and may be as great as 2000 D or greater, but usually does not exceed about 5000 D.

The targeted bifunctional molecule is further characterized in that it exhibits a modulated or different biodistribution upon administration to a host as compared to free drug control. By modulated biodistribution is meant that the bifunctional molecule is distributed differently throughout a host to which it is administered as compared to the corresponding free drug (i.e. drug that is not conjugated to another moiety, e.g. a targeting moiety as is found in the subject bifunctional molecules) of the bifunctional molecule. For example, a bifunctional molecule of the subject invention may be found primarily in neoplastic cells following administration to a host where its corresponding free drug will be found systemically throughout the host, i.e. in all proliferating cells and not just neoplastic cells. In evaluating whether a given bifunctional molecule has a modified biodistribution, the biodistribution is typically assessed at a time at least 1 week, usually at least 3 days and more usually at least 1 day following administration, but preferably within about 6 hrs and more preferably within about 1 hr following administration. In many embodiments, the subject targeted bifunctional molecules exhibit at least one of improved efficacy and reduced toxicity as compared to their free drug controls. By improved efficacy is meant an efficacy that is at least about 2 fold, usually at least about 4 fold and more usually at least about 10 fold greater than the corresponding free drug control. By reduced toxicity is meant a toxicity that is at least about 2 fold, usually at least about 4 fold and in many embodiments at least 10 fold lower than the corresponding free drug.

Targeted bifunctional molecules of the subject invention are generally described by the formula:

wherein:
X is a drug moiety;
L is bond or linking group; and
Z is targeting moiety;
with the proviso that X and Z are different.

Drug Moiety: X

The drug moiety X may be any molecule, as well as binding portion or fragment thereof, that is capable of modulating a biological process in a living host, either by itself or in the context of the biodistribution modulating protein/bifunctional molecule binary complex. Generally, X is a small organic molecule that is capable of binding to the target of interest. As the drug moiety of the bifunctional molecule is a small molecule, it generally has a molecular weight of at least about 50 D, usually at least about 100 D, where the molecular weight may be as high as 500 D or higher, but will usually not exceed about 2000 D.

The drug moiety is capable of interacting with a target in the host into which the bifunctional molecule is administered during practice of the subject methods. The target may be a number of different types of naturally occurring structures, where targets of interest include both intracellular and extracellular targets where such targets may be proteins, phospholipids, nucleic acids and the like, where proteins are of particular interest. Specific proteinaceous targets of interest include, without limitation, enzymes, e.g. kinases, phosphatases, reductases, cyclooxygenases, proteases and the like, targets comprising domains involved in protein-protein interactions such as the SFH2, SH3, PTB and PDZ domains, structural proteins, e.g. actin, tubulin, etc., membrane receptors, immunoglobulins, e.g. IgE, cell adhesion receptors, such as integrins, etc., ion channels, transmembrane pumps, transcription factors, signaling proteins, and the like.

The drug moiety of the bifunctional compound will include one or more functional groups necessary for structural interaction with the target, e.g. groups necessary for hydrophobic, hydrophilic, electrostatic or even covalent interactions depending on the particular drug and its intended target. Where the target is a protein, the drug moiety will include functional groups necessary for structural interaction with proteins, such as hydrogen bonding, hydrophobic-hydrophobic interactions, electrostatic interactions, etc., and will typically include at least an amine, amide, sulfhydryl, carbonyl, hydroxyl or carboxyl group, preferably at least two of the functional chemical groups. As described in greater detail below, the drug moiety will also comprise a region that may be modified and/or participate in covalent linkage to the other components of the bifunctional molecule, such as the targeting moiety or linker, without substantially adversely affecting the moiety's ability to bind to its target.

The drug moieties often comprise cyclical carbon or heterocyclic structures and/or aromatic or polyaromatic structures substituted with one or more of the above functional groups. Also of interest as drug moieties are structures found among biomolecules, including peptides, saccharides, fatty acids, steroids, purines, pyrimidines, derivatives, structural analogs or combinations thereof. Such compounds may be screened to identify those of interest where a variety of different screening protocols are known in the art.

The drug moiety of the bifunctional molecule may be derived from a naturally occurring or synthetic compound that may be obtained from a wide variety of sources including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As such, the drug moiety may be obtained from a library of naturally occurring or synthetic molecules, including a library of compounds produced through combinatorial means, i.e. a compound diversity combinatorial library. When obtained from such libraries, the drug moiety employed will have demonstrated some desirable activity in an appropriate screening assay for the activity. Combinatorial libraries, as well as methods for the production and screening, are known in the art and described in U.S. Pat. Nos. 5,741,713; 5,734,018; 5,731,423; 5,721,099; 5,708,153; 5,698,673: 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Specific drugs of interest from which the drug moiety may be derived include, but are not limited to: psychopharmacological agents, such as (1) central nervous system depressants, e.g. general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines. etc.), central voluntary muscle tone modifying drugs (anticonvulsants, such as hydantoins, barbiturates, oxazolidinediones, succinimides, acylureides, glutarimides, benzodiazepines, secondary and tertiary alcohols, dibenzazepine derivatives, valproic acid and derivatives, GABA analogs. etc.), analgesics (morphine and derivatives, oripavine derivatives, morphinan derivatives, phenylpiperidines, 2,6-methane-3-benzazocaine derivatives, diphenylpropylamines and isosteres, salicylates, p-aminophenol derivatives, 5-pyrazolone derivatives, arylacetic acid derivatives, fenamates and isosteres, etc.) and antiemetics (anticholinergics, antihistamines, antidopaminergics, etc.). (2) central nervous system stimulants, e.g. analeptics (respiratory stimulants, convulsant stimulants, psychomotor stimulants), narcotic antagonists (morphine derivatives, oripavine derivatives, 2,6-methane-3-benzoxacine derivatives, morphinan derivatives) nootropics, (3) psychopharmacologicals, e.g. anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives. etc.), antidepressants (tricyclic compounds, MAO inhibitors. etc.). (4) respiratory tract drugs. e.g. central antitussives (opium alkaloids and their derivatives):

pharmacodynamic agents, such as (1) peripheral nervous system drugs, e.g. local anesthetics (ester derivatives, amide derivatives), (2) drugs acting at synaptic or neuroeffector junctional sites, e.g. cholinergic agents, cholinergic blocking agents, neuromuscular blocking agents, adrenergic agents, antiadrenergic agents, (3) smooth muscle active drugs, e.g. spasmolytics (anticholinergics, musculotropic spasmolytics), vasodilators, smooth muscle stimulants, (4) histamines and antihistamines, e.g. histamine and derivative thereof (betazole), antihistamines ($H_1$-antagonists, $H_2$-antagonists), histamine metabolism drugs, (5) cardiovascular drugs. e.g. cardiotonics (plant extracts, butenolides, pentadienolids, alkaloids from erythrophleum species, ionophores, adrenoceptor stimulants, etc), antiarrhythmic drugs, antihypertensive agents, antilipidemic agents (clofibric acid derivatives, nicotinic acid derivatives, hormones and analogs. antibiotics, salicylic acid and derivatives), antivaricose drugs, hemostyptics, (6) blood and hemopoietic system drugs, e.g. antianemia drugs, blood coagulation drugs (hemostatics, anticoagulants, antithrombotics, thrombolytics, blood proteins and their fractions), (7) gastrointestinal tract drugs, e.g. digestants (stomachics, choleretics), antiulcer drugs, antidiarrheal agents, (8) locally acting drugs; chemotherapeutic agents, such as (1) anti-infective agents, e.g. ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, etc., and (2) cytostatics, i.e. antineoplastic agents or cytotoxic drugs, such as alkylating agents, e.g. Mechlorethamine hydrochloride (Nitrogen Mustard, Mustargen, HN2). Cyclophosphamide (Cytovan, Endoxana), Ifosfamide (IFEX), Chlorambucil (Leukeran), Melphalan (Phenylalanine Mustard, L-sarcolysin, Alkeran, L-PAM), Busulfan (Myleran), Thiotepa (Triethylenethiophosphoramide), Carmustine (BiCNU, BCNU), Lomustine (CeeNU, CCNU), Streptozocin (Zanosar) and the like; plant alkaloids, e.g. Vincristine (Oncovin), Vinblastine (Velban, Velbe), Paclitaxel (Taxol), and the like: antimetabolites, e.g. Methotrexate (MTX), Mercaptopurine (Purinethol, 6-MP). Thioguanine (6-TG), Fluorouracil (5-F1U). Cytarabine (Cytosar-U, Ara-C), Azacitidine (Mylosar, 5-AZA) and the like: antibiotics. e.g. Dactinomycin (Actinomycin D. Cosmegen), Doxorubicin (Adriamycin), Daunorubicin (duanomycin, Cerubidine), Idarubicin (Idamycin), Bleomycin (Blenoxane), Picamycin (Mithramycin, Mithracin), Mitomycin (Mutamycin) and the like, and other anticellular proliferative agents, e.g. Hydroxyurea (Hydrea), Procarbazine (Mutalane), Dacarbazine (DTIC-Dome). Cisplatin (Platinol) Carboplatin (Paraplatin), Asparaginase (Elspar) Etoposide (VePesid, VP-16-213). Amsarcrine (AMSA, m-AMSA), Mitotane (Lysodren), Mitoxantrone (Novatrone). and the like;

Antibiotics, such as: aminoglycosides. e.g. amikacin, apramycin, arbekacin, bambermycins, butirosin, dibekacin, dihydrostreptomycin, fortimicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g. azidamfenicol, chloramphenicol, florfenicol, and theimaphenicol: ansamycins, e.g. rifamide, rifampin, rifamycin, rifapentine, rifaximin; β-lactams, e.g. carbacephems, carbapenems, cephalosporins, cehpamycins, monobactams, oxaphems, penicillins: lincosamides, e.g. clinamycin, lincomycin: macrolides, e.g. clarithromycin, dirthromycin, erythromycin, etc.; polypeptides, e.g. amphomycin, bacitracin, capreomycin, etc.; tetracyclines, e.g. apicycline, chlortetracycline, clomocycline, etc.; synthetic antibacterial agents, such as 2,4-diaminopyrimidines, nitrofurans, quinolones and analogs thereof, sulfonamides, sulfones;

Antifungal agents, such as: polyenes, e.g. amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g. butenafine, naftifine, terbinafine; imidazoles, e.g. bifonazole, butoconazole, chlordantoin, chlormidazole, etc., thiocarbamates, e.g. tolciclate, triazoles, e.g. fluconazole, itraconazole, terconazole;

Anthelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, diethylcarbamazine, etc.;

Antimalarials, such as: acedapsone, amodiaquin, arteether, artemether, artemisinin, artesunate, atovaquone, bebeerine, berberine, chirata, chlorguanide, chloroquine, chlorprogaunil, cinchona, cinchonidine, cinchonine, cycloguanil, gentiopicrin, halofantrine, hydroxy chloroquine, mefloquine hydrochloride, 3-methylarsacetin, pamaquine, plasmocid, primaquine, pyrimethamine, quinacrine, quinidine, quinine, quinocide, quinoline, dibasic sodium arsenate:

Antiprotozoan agents, such as: acranil, tinidazole, ipronidazole, ethylstibamine, pentamidine, acetarsone, aminitrozole, anisomycin, nifuratel, tinidazole, benzidazole, suramin, and the like.

Name brand drugs of interest include, but are not limited to: Rezulin™, Lovastatin™, Enalapril™, Prozac™, Prilosec™, Lipotor™, Claritin™, Zocor™, Ciprofloxacin™, Viagra™, Crixivan™, Ritalin™, and the like.

Drug compounds of interest from which drug moieties may be derived are also listed in: Goodman & Gilman's. The Pharmacological Basis of Therapeutics (9th Ed) (Goodman et al. eds) (McGraw-Hill) (1996), and 1999 Physician's Desk Reference (1998).

Specific compounds of interest also include, but are not limited to:

antineoplastic agents, as disclosed in U.S. Pat. Nos. 5,880,161, 5,877,206, 5,786,344, 5,760,041, 5,753,668, 5,698,529, 5,684,004, 5,665,715, 5,654,484, 5,624,924, 5,618,813, 5,610,292, 5,597,831, 5,530,026, 5,525,633, 5,525,606, 5,512,678, 5,508,277, 5,463,181, 5,409,893, 5,358,952, 5,318,965, 5,223,503, 5,214,068, 5,196,424, 5,100,924, 5,101,072, 5,077,404, 5,071,848, 5,066,493, 5,019,390, 4,996,229, 4,996,206, 4,970,318, 4,968,800, 4,962,114, 4,927,828, 4,892,887, 4,889,859, 4,886,790, 4,882,334, 4,882,333, 4,871,746, 4,863,955, 4,849,563, 4,845,216, 4,833,145, 4,824,955, 4,785,085, 4,76,925, 4,684,747, 4,618,685, 4,611,066, 4,550,186, 4,550,186, 4,544,501, 4,541,956, 4,532,327, 4,490,540, 4,390,283, 4,391,982, 4,383,994, 4,294,763, 4,283,394, 4,24,411, 4,214,089, 4,150,231, 4,147,708, 4,056,673, 4,029,661, 4,012,448;

psycopharmacological/psychotropic agents, as disclosed in U.S. Pat. Nos. 5,192,799, 5,036,070, 4,778,800, 4,753,951, 4,590,180, 4,690,930, 4,645,773, 4,427,694, 4,424,202, 4,440,781, 5,686,482, 5,478,828, 5,461,062, 5,387,593, 5,387,586, 5,256,664, 5,192,799, 5,120,733, 5,036,070, 4,977,167, 4,904,663, 4,788,188, 4,778,800, 4,753,951, 4,690,930, 4,645,773, 4,631,285, 4,617,314, 4,613,600, 4,590,180, 4,560,684, 4,548,938, 4,529,727, 4,459,306, 4,443,451, 4,440,781, 4,427,694, 4,424,202, 4,397,853, 4,358,451, 4,324,787, 4,314,081, 4,313,896, 4,294,828, 4,277,476, 4,267,328, 4,264,499, 4,231,930, 4,194,009, 4,188,388, 4,148,796, 4,128,717, 4,062,858, 4,031,226, 4,020,072, 4,018,895, 4,018,779, 4,013,672, 3,994,898, 3,968,125, 3,939,152, 3,928,356, 3,880,834, 3,668,210;

cardiovascular agents, as disclosed in U.S. Pat. Nos. 4,966,967, 5,661,129, 5,552,411, 5,332,737, 5,389,675, 5,198,449, 5,079,247, 4,966,967, 4,874,760, 4,954,526, 5,051,423, 4,888,335, 4,853,391, 4,906,634, 4,775,757, 4,727,072, 4,542,160, 4,522,949, 4,524,151, 4,525,479, 4,474,804, 4,520,026, 4,520,026, 5,869,478, 5,859,239, 5,837,702, 5,807,889, 5,731,322, 5,726,171, 5,723,457, 5,705,523, 5,696,111, 5,691,332, 5,679,672, 5,661,129, 5,654,294, 5,646,276, 5,637,586, 5,631,251, 5,612,370, 5,612,323, 5,574,037, 5,563,170, 5,552,411, 5,552,397, 5,547,966, 5,482,925, 5,457,118, 5,414,017, 5,414,013, 5,401,758, 5,393,771, 5,362,902, 5,332,737, 5,310,731, 5,260,444, 5,223,516, 5,217,958, 5,208,245, 5,202,330, 5,198,449, 5,189,036, 5,185,362, 5,140,031, 5,128,349, 5,116,861, 5,079,247, 5,070,099, 5,061,813, 5,055,466, 5,051,423, 5,036,065, 5,026,712, 5,011,931, 5,006,542, 4,981,843, 4,977,144, 4,971,984, 4,966,967, 4,959,383, 4,954,526, 4,952,692, 4,039,137, 4,906,634, 4,889,866, 4,888,335, 4,883,872, 4,883,811, 4,847,379, 4,835,157, 4,824,831, 4,780,538, 4,775,757, 4,774,239, 4,771,047, 4,769,371, 4,767,756, 4,762,837, 4,753,946, 4,752,616, 4,749,715, 4,738,978, 4,735,962, 4,734,426, 4,734,425, 4,734,424, 4,730,052, 4,727,072, 4,721,796, 4,707,550, 4,704,382, 4,703,120, 4,681,970, 4,681,882, 4,670,560, 4,670,453, 4,668,787, 4,663,337, 4,663,336, 4,661,506, 4,656,267, 4,656,185, 4,654,357, 4,654,356, 4,654,355, 4,654,335, 4,652,578, 4,652,576, 4,650,874, 4,650,797, 4,649,139, 4,647,585, 4,647,573, 4,647,565, 4,647,561, 4,645,836, 4,639,461, 4,638,012, 4,638,011, 4,632,931, 4,631,283, 4,628,095, 4,626,548, 4,614,825, 4,611,007, 4,611,006, 4,611,005, 4,609,671, 4,608,386, 4,607,049, 4,607,048, 4,595,692, 4,593,042, 4,593,029, 4,591,603, 4,588,743, 4,588,742, 4,588,741, 4,582,854, 4,575,512, 4,568,762, 4,560,698, 4,556,739, 4,556,675, 4,555,571, 4,555,570, 4,555,523, 4,550,120, 4,542,160, 4,542,157, 4,542,156, 4,542,155, 4,542,151, 4,537,981, 4,537,904, 4,536,514, 4,536,513, 4,533,673, 4,526,901, 4,526,900, 4,525,479, 4,524,151, 4,522,949, 4,521,539, 4,520,026, 4,517,188, 4,482,562, 4,474,804, 4,474,803, 4,472,411, 4,466,979, 4,463,015, 4,456,617, 4,456,616, 4,456,615, 4,418,076, 4,416,896, 4,252,815, 4,220,594, 4,190,587, 4,177,280, 4,164,586, 4,151,297, 4,145,443, 4,143,054, 4,123,550, 4,083,968, 4,076,834, 4,064,259, 4,064,258, 4,064,257, 4,058,620, 4,001,421, 3,993,639, 3,991,057, 3,982,010, 3,980,652, 3,968,117, 3,959,296, 3,951,950, 3,933,834, 3,925,369, 3,923,818, 3,898,210, 3,897,442, 3,897,441, 3,886,157, 3,883,540, 3,873,715, 3,867,383, 3,873,715, 3,867,383, 3,691,216, 3,624,126;

antimicrobial agents as disclosed in U.S. Pat. Nos. 5,902,594, 5,874,476, 5,874,436, 5,859,027, 5,856,320, 5,854,242, 5,811,091, 5,786,350, 5,783,177, 5,773,469, 5,762,919, 5,753,715, 5,741,526, 5,709,870, 5,707,990, 5,696,117, 5,684,042, 5,683,709, 5,656,591, 5,643,971, 5,643,950, 5,610,196, 5,608,056, 5,604,262, 5,595,742, 5,576,341, 5,554,373, 5,541,233, 5,534,546, 5,534,508, 5,514,715, 5,508,417, 5,464,832, 5,428,073, 5,428,016, 5,424,396, 5,399,553, 5,391,544, 5,385,902, 5,359,066, 5,356,803, 5,354,862, 5,346,913, 5,302,592, 5,288,693, 5,266,567, 5,254,685, 5,252,745, 5,209,930, 5,196,441, 5,190,961, 5,175,160, 5,157,051, 5,096,700, 5,093,342, 5,089,251, 5,073,570, 5,061,702, 5,037,809, 5,036,077, 5,010,109, 4,970,226, 4,916,156, 4,888,434, 4,870,093, 4,855,318, 4,784,991, 4,746,504, 4,686,221, 4,599,228, 4,552,882, 4,492,700, 4,489,098, 4,489,085, 4,487,776, 4,479,953, 4,477,448, 4,474,807, 4,470,994, 4,370,484, 4,337,199, 4,311,709, 4,308,283, 4,304,910, 4,260,634, 4,233,311, 4,215,131, 4,166,122, 4,141,981, 4,130,664, 4,089,977, 4,089,900, 4,069,341, 4,055,655, 4,049,665, 4,044,139, 4,002,775, 3,991,201, 3,966,968, 3,954,868, 3,936,393, 3,917,476, 3,915,889, 3,867,548, 3,865,748, 3,867,548, 3,865,748, 3,783,160, 3,764,676, 3,764,677;

anti-inflammatory agents as disclosed in U.S. Pat. Nos. 5,872,109, 5,837,735, 5,827,837, 5,821,250, 5,814,648, 5,780,026, 5,776,946, 5,760,002, 5,750,543, 5,741,798, 5,739,279, 5,733,939, 5,723,481, 5,716,967, 5,688,949, 5,686,488, 5,686,471, 5,686,434, 5,684,204, 5,684,041, 5,684,031, 5,684,002, 5,677,318, 5,674,891, 5,672,620, 5,665,752, 5,656,661, 5,635,516, 5,631,283, 5,622,948, 5,618,835, 5,607,959, 5,593,980, 5,593,060, 5,580,888, 5,552,424, 5,552,422, 5,516,764, 5,510,361, 5,508,026, 5,500,417, 5,498,405, 5,494,927, 5,476,876, 5,472,973 5,470,885, 5,470,842, 5,464,856, 5,464,849 5,462,952, 5,459,151, 5,451,686, 5,444,043, 5,436,265, 5,432,181, RE034,918, 5,393,756, 5,380,738, 5,376,670, 5,360,811, 5,354,768, 5,348,957, 5,347,029, 5,340,815, 5,338,753, 5,324,648, 5,319,099, 5,318,971, 5,312,821, 5,302,597, 5,298,633, 5,298,522, 5,298,498, 5,290,800, 5,290,788, 5,284,949, 5,280,045, 5,270,319, 5,266,562, 5,256,680, 5,250,700, 5,250,552, 5,248,682, 5,244,917, 5,240,929, 5,234,939, 5,234,137, 5,232,939, 5,225,571, 5,225,418, 5,220,025, 5,212,189, 5,212,172, 5,208,250, 5,204,365, 5,202,350, 5,196,431, 5,191,084, 5,187,175, 5,185,326, 5,183,906, 5,177,079, 5,171,864, 5,169,963, 5,155,122, 5,143,929, 5,143,928, 5,143,927, 5,124,455, 5,124,347, 5,114,958, 5,112,846, 5,104,656, 5,098,613, 5,095,037, 5,095,019, 5,086,064, 5,081,261, 5,081,147, 5,081,126, 5,075,330, 5,066,668, 5,059,602, 5,043,457, 5,037,835, 5,037,811, 5,036,088, 5,013,850, 5,013,751, 5,013,736, 500654, 4,992,448, 4,992,447, 4,988,733, 4,988,728, 4,981, 865, 4,962,119, 4,959,378, 4,954,519, 4,945,009, 4,942,236, 4,931,457, 4,927,835, 4,912,248, 4,910,192, 4,904,786, 4,904,685, 4,904,674, 4,904,671, 4,897,397, 4,895,953, 4,891,370, 4,870,210, 4,859,686, 4,857,644, 4,853,392, 4,851,412, 4,847,303, 4,847,290, 4,845,242, 4,835,166, 4,826,990, 4,803,216, 4,801,598, 4,791,129, 4,788,205, 4,778,818, 4,775,679, 4,772,703, 4,767,776, 4,764,525, 4,760,051, 4,748,153, 4,725,616, 4,721,712, 4,713,393, 4,708,966, 4,695,571, 4,686,235, 4,686,224, 4,680,298, 4,678,802, 4,652,564, 4,644,005, 4,632,923, 4,629,793, 4,614,741, 4,599,360, 4,596,828, 4,595,694, 4,595,686, 4,594,357, 4,585,755, 4,579,866, 4,578,390, 4,569,942, 4,567,201, 4,563,476, 4,559,348, 45580 67, 4,556,672, 4,556,669, 4,539,326, 4,537,903, 453503, 4,518,608, 4,514, 415, 4,512,990, 4,501,755, 4,495,197, 4,493,839, 4,465,687, 4,440,779, 4,440,763, 4,435,420, 4,412,995, 4,400,534, 4,355,034, 4,335,141, 4,322,420, 4,275,064, 4,244,963, 4,235,908, 4,234,593, 4,226,887, 4,201,778, 4,181,720, 4,173,650, 4,173,634, 4,145,444, 4,128,664, 4,125,612, 4,124,726, 4,124,707, 4,117,135, 4,027,031, 4,024,284, 4,021,553, 4,021,550, 4,018,923, 4,012,527, 4,011,326, 3,998,970, 3,998,954, 3,993,763, 3,991,212, 3,984,405, 3,978,227, 3,978,219, 3,978,202, 3,975,543, 3,968,224, 3,959,368, 3,949,082, 3,949,081, 3,947,475, 3,936,450, 3,934,018, 3,930,005, 3,857,955, 3,856,962, 3,821,377, 3,821,401, 3,789,121, 3,789,123, 3,726,978, 3,694,471, 3,691,214, 3,678,169, 3,624,216;

immunosuppressive agents, as disclosed in U.S. Pat. Nos. 4,450,159, 4,450,159, 5,905,085, 5,883,119, 5,880,280, 5,877,184, 5,874,594, 5,843,452, 5,817,672, 5,817,661, 5,817,660, 5,801,193, 5,776,974, 5,763,478, 5,739,169, 5,723,466, 5,719,176, 5,696,156, 5,695,753, 5,603,648, 563645, 5,691,346, 5,686,469, 5,686,424, 5,679,705, 5,670, 640, 5,670,504, 5,665,774, 5,665,772, 5,648,376, 5,639,455, 5,633,277, 5,624,930, 5,622,970, 5,605,903, 5,604,229, 5,574,041, 5,565,560, 5,550,233, 5,545,734, 5,540,931, 5,532,248, 5,527,820, 5,516,797, 5,514,688, 5,512,687, 5,506,233, 5,506,228, 5,494,895, 5,484,788, 5,470,857, 5,464,615, 5,432,183, 5,431,896, 5,385,918, 5,349,061, 5,344,925, 5,330,993, 5,308,837, 5,290,783, 5,290,772, 5,284,877, 5,284,840, 5,273,979, 526533, 526300, 5,252,732, 5,250,678, 5,247,076, 5,244,896, 5,238,689, 5,219,884, 5,208,241, 5,208,228, 5,202,332, 5,192,773, 5,189,042, 5,160,851, 5,162,334, 5,151,413, 5,149,701, 5,147,877, 5,143,918, 5,138,051, 5,093,338, 5,091,389, 5,068,323, 5,068,247, 5,064,835, 5,061,728, 5,055,290, 4,981,792, 4,810,692, 4,410,696, 4,346,096, 4,342,769, 4,317,825, 4,256,766, 4,180,588, 4,000,275, 3,759,921;

analgesic agents, as disclosed in U.S. Pat. Nos. 5,292,736, 5,688,825, 5,554,789, 5,455,230, 5,292,736, 5,298,522, 5,216,165, 5,438,064, 5,204,365, 5,017,578, 4,906,655, 4,906,655, 4,994,450, 4,749,792, 4,980,365, 4,794,110, 4,670,541, 4,737,493, 4,622,326, 4,536,512, 4,719,231, 4,533,671, 4,552,866, 4,539,312, 4,569,942, 4,681,879, 4,511,724, 4,556,672, 4,721,712, 4,474,806, 4,595,686, 4,440,779, 4,434,175, 4,608,374, 4,395,402, 4,400,534, 4,374,139, 4,361,583, 4,252,816, 4,251,530, 5,874,459, 5,688,825, 5,554,789, 5,455,230, 5,438,064, 5,298,522, 5,216,165, 5,204,365, 5,030,639, 5,017,578, 5,008,264, 4,994,450, 4,980,365, 4,906,655, 4,847,290, 4,844,907, 4,794,110, 4,791,129, 4,774,256, 4,749,792, 4,737,493, 4,721,712, 4,719,231, 4,681,879, 4,670,541, 4,667,039, 4,658,037, 4,634,708, 4,623,648, 4,622,326, 4,608,374, 4,595,686, 4,594,188, 4,569,942, 4,556,672, 4,552,866, 4,539,312, 4,536,512, 4,533,671, 4,511,724, 4,440,779, 4,434,175, 4,400,534, 4,395,402, 4,391,827, 4,374,139, 4,361,583, 4,322,420, 4,306,097, 4,252,816, 4,251,530, 4,244,955, 4,232,018, 4,209,520, 4,164,514, 4,147,872, 4,133,819, 4,124,713, 4,117,012, 4,064,272, 4,022,836, 3,966,944;

cholinergic agents as disclosed in U.S. Pat. Nos. 5,219,872, 5,219,873, 5,073,560, 5,073,560, 5,346,911, 5,424,301, 5,073,560, 5,219,872, 4,900,748, 4,786,648, 4,798,841, 4,782,071, 4,710,508, 5,482,938, 5,464,842, 5,378,723, 5,346,911, 5,318,978, 5,219,873, 5,219,872, 5,084,281, 5,073,560, 5,002,955, 4,988,710, 4,900,748, 4,798,841, 4,786,648, 4,782,071, 4,745,123, 4,710,508;

adrenergic agents as disclosed in U.S. Pat. Nos. 5,091,528, 5,091,528, 4,835,157, 5,708,015, 5,594,027, 5,580,802, 5,576,332, 5,510,376, 5,482,961, 5,334,601, 5,202,347, 5,135,926, 5,116,867, 5,091,528, 5,017,618, 4,835,157, 4,829,086, 4,579,867, 4,568,679, 4,469,690, 4,395,559, 4,381,309, 4,363,808, 4,343,800, 4,329,289, 4,314,943, 4,311,708, 4,304,721, 4,296,117, 4,285,873, 4,281,189, 4,278,608, 4,247,710, 4,145,550, 4,145,425, 4,139,535, 4,082,843, 4,011,321, 4,001,421, 3,982,010, 3,940,407, 3,852,468, 3,832,470;

antihistamine agents, as disclosed in U.S. Pat. Nos. 5,874, 479, 5,863,938, 5,856,364, 5,770,612, 5,702,688, 5,674,912, 5,663,208, 5,658,957, 5,652,274, 5,648,380, 5,646,190, 5,641,814, 5,633,285, 5,614,561, 5,602,183, 4,923,892, 4,782,058, 4,393,210, 4,180,583, 3,965,257, 3,946,022, 3,931,197;

steroidal agents as disclosed in U.S. Pat. Nos. 5,863,538, 5,855,907, 5,855,866, 5,780,592, 5,776,427, 5,651,987, 5,346,887, 5,256,408, 5,252,319, 5,209,926, 4,996,335, 4,927,807, 4,910,192, 4,710,495, 4,049,805, 4,004,005, 3,670,079, 3,608,076, 5,892,028, 5,888,995, 5,883,087, 5,880,115, 5,869,475, 5,866,558, 5,861,390, 5,861,388, 5,854,235, 5,837,698, 5,834,452, 5,830,886, 5,792,758, 5,792,757, 5,763,361, 5,744,462, 5,741,787, 5,741,786, 5,733,899, 5,731,345, 5,723,638, 5,721,226, 5,712,264, 5,712,263, 5,710,144, 5,707,984, 5,705,494, 5,700,793, 5,698,720, 5,698,545, 5,696,106, 5,677,293, 5,674,861, 5,661,141, 5,656,621, 5,646,136, 5,637,691, 5,616,574, 5,614,514, 5,604,215, 5,604,213, 5,599,807, 5,585,482, 5,565,588, 5,563,259, 5,563,131, 5,561,124, 5,556,845, 5,547,949, 5,536,714, 5,527,806, 5,506,354, 5,506,221, 5,494,907, 5,491,136, 5,478,956, 5,426,179, 5,422,262, 5,391,776, 5,382,661, 5,380,841, 5,380,840, 5,380,839, 5,373,095, 5,371,078, 5,352,809, 5,344,827, 5,344,826, 5,338,837, 5,336,686, 5,292,906, 5,202,878, 5,281,587, 5,272,140, 5,244,886, 5,236,912, 5,232,915, 5,219,879, 5,218,109, 5,215,972, 5,212,166, 5,206,415, 5,194,602, 5,166,201, 5,166,055, 5,126,488, 5,116,829, 5,108,996, 5,099,037, 5,096,892, 5,093,502, 5,086,047, 5,084,450, 5,082,835, 5,081,114, 5,053,404, 5,041,433, 5,041,432, 5,034,548, 5,032,586, 5,026,882, 4,996,335, 4,975,537, 4,970,205, 4,954,446, 4,950,428, 4,946,834, 4,937,237, 4,921,846, 4,920,099, 4,910,226, 4,900,725, 4,892,867, 4,888,336, 4,885,280, 4,882,322, 4,882,319, 4,882,315, 4,874,855, 4,868,167, 4,865,767, 4,861,875, 4,861,765, 4,861,763, 4,847,014, 4,774,236, 4,753,932, 4,711,856, 4,710,495, 4,701,450, 4,701,449, 4,689,410, 4,680,290, 4,670,551, 4,664,850, 4,659,516, 4,647,410, 4,634,695, 4,634,693, 4,588,530, 4,567,000, 4,560,557, 4,558,041, 4,552,871, 4,552,868, 4,541,956, 4,519,946, 4,515,787, 4,512,986, 4,502,989, 4,495,102;

the disclosures of which are herein incorporated by reference.

The drug moiety of the bifunctional molecule may be the whole compound or a derivative thereof e.g. a binding fragment or portion thereof, that retains its affinity and specificity for the target of interest, and therefor its desired activity while having a linkage site for covalent bonding to the targeting moiety or linker.

Targeting Moiety: Z

Z is a targeting moiety that directs the bifunctional molecule to the host site(s) of interest, e.g. through binding to a biodistribution modulating protein in the host into which the targeted bifunctional molecule is to be administered. In many embodiments, the targeting moiety of the subject bifunctional molecules binds to a specific biodistribution modulating protein present in the host. The binding interaction between the targeting moiety and the biodistribution modulating protein is non-covalent, such that no covalent bonds are produced between the bifunctional molecule and the biodistribution modulating protein upon binding of the two entities. As the targeting moiety of the bifunctional molecule is a small molecule, it generally has a molecular weight of at least about 50 D. usually at least about 100 D. where the molecular weight may be as high as 500 D) or higher, but will usually not exceed about 2000 D. The targeting moiety, in the context of the bifunctional molecule, has substantially no pharmacological activity at its effective concentration beyond binding to its corresponding biodistribution modulating protein, i.e. it does not directly cause a biodistribution modulating protein-mediated pharmacological event to occur upon binding at its effective concentration to the biodistribution modulating protein, where a biodistribution modulating protein mediated pharmacological event is a pharmacologically relevant event which is directly modulated by the biodistribution modulating protein in the absence of the subject bifunctional molecules.

In other certain embodiments, the modulating moiety may have some pharmacological activity, where this pharmacological activity does not adversely effect the host to the extent that the therapy in which the bifunctional molecule is employed places the host in a worst condition than prior to the therapy. In other words, pharmacological activity in the modulating moiety may be tolerated in these embodiments to the extent that any consequences of such activity, if any, are outweighed by the benefits provided by the bifunctional molecule. As used herein, pharmacological event is an event that is distinct from a biochemical event (e.g. inhibition a prolyl isomerase activity) or a biological event (e.g. inducement of a cell to express new genes).

The biodistribution modulating protein to which the targeting moiety of the bifunctional molecule binds may be any protein that is present in the host at the time the bifunctional molecule is introduced to the host, i.e. the biodistribution modulating protein will be endogenous to the host. The biodistribution modulating protein may or may not have one or more modified residues, e.g. residues that are glycosylated, such that the it may or may not be a glycoprotein. Furthermore, the biodistribution modulating protein to which the bifunctional molecule is targeted via the targeting moiety may or may not be part of a complex or structure of a plurality of biological molecules, e.g. lipids, where such complexes or structures may include lipoproteins, lipid bilayers, and the like. However, in many embodiments, the biodistribution modulating protein to which the bifunctional molecule is targeted will be by itself, i.e. will not be part of a larger structure of a plurality of biological molecules. Though the biodistribution modulating protein may be a protein that is not native to the host but has been introduced at some time prior to introduction of the bifunctional molecule, e.g. through prior administration of the protein or a nucleic acid composition encoding the same such as through gene therapy, the biodistribution modulating protein will, in many embodiments, be a protein that is native to and naturally expressed by at least some of the host's cells. i.e. a naturally occurring protein in the host. The biodistribution modulating protein is a protein that is present in the region of host occupied by the drug target. As such, where the drug target is an intracellular drug target. the biodistribution protein will be an intracellular protein present in the cell comprising the target, typically expressed in the cell comprising the target, i.e. the biodistribution modulating protein and target are co-expressed in the same cell. Likewise, where the drug target is an extracellular drug target, the biodistribution modulating protein will be an extracellular protein that is found in the vicinity of the target.

Although not a requirement in certain embodiments, in many preferred embodiments the biodistribution modulating protein is one that is present in the host in sufficient quantities such that, upon binding of at least a portion of biodistribution modulating protein present in the host to the bifunctional molecule, adverse pharmacological effects do not occur. In other words, the biodistribution modulating protein in these preferred embodiments is one in which its native and desirable biological activity, if any, is not diminished by an unacceptable amount following binding of the portion of the biodistribution modulating protein population to the bifunctional molecule. The amount of diminished activity of the biodistribution modulating protein that is acceptable in a given situation is determined with respect to the condition being treated in view of the benefits of treatment versus the reduction of overall biodistribution modulating protein activity, if any. In certain situations, a large decrease in overall biodistribution modulating protein activity may be acceptable, e.g. where the biodistribution modulating protein activity aggravates the condition being treated.

The specific biodistribution modulating protein to which the targeting moiety binds may vary greatly depending on the desired biodistribution of the bifunctional molecule and drug moiety component thereof. For example, where one wishes to direct the bifunctional molecule to an intracellular space. intracellular biodistribution modulating proteins of interest include: peptidyl-prolyl isomerases, e.g. FKBPs and cyclophilins; ubiquitously expressed molecular chaperones, e.g.

Heat Shock Protein 90 (Hsp90) steroid hormone receptors, e.g. estrogen receptors, glucocorticoid receptors. androgen receptors: retinoic acid binding protein, cytoskeletal proteins, such as tubulin and actin: etc. Of particular interest as intracellular biodistribution modulating proteins are cis-trans peptidyl-prolyl isomerases which interact with many proteins because of their chaperonin/isomerase activity, e.g. FKBPs and cyclophilins, Peptidyl-prolyl isomerases of interest include FKBPs. A number of different FKBPs are known in the art, and include those described in: Sabatini et al., Mol. Neurobiol. (October 1997) 15:223-239: Marks. Physiol. Rev. (July 1996) 76:631-649: Kay. Biochem J. (March. 1996) 314: 361-385; Braun et al., FASEB J. (January 1995) 9:63-72: Fruman et al, FASEB J. (April 1994) 8:391-400: and Hacker et al., Mol. Microbiol. (November 1993) 10: 445-456. FKBPs of interest include FKBP 12, FKBP 52, FKBP 14.6 (described in U.S. Pat. No. 5,525,523, the disclosure of which is herein incorporated by reference): FKBP 12.6 (described in U.S. Pat. No. 5,457,182 the disclosure of which is herein incorporated by reference); FKBP 13 (described in U.S. Pat. No. 5,498,597, the disclosure of which is herein incorporated by reference): and HCB (described in U.S. Pat. No. 5,196,352 the disclosure of which is herein incorporated by reference): where FKBP 12 and FKBP 52 are of particular interest as intracellular biodistribution modulating proteins. Also of specific interest as intracellular biodistribution modulating proteins are cyclophilins. A number of cyclophilins are known in the art and are described in Trandinh et al., FASEB J. (December 1992) 6: 3410-3420: Harding et al., Transplantation (August 1988) 46: 29S-35S. Specific cyclophilins of interest as intracellular biodistribution modulating proteins include cyclophilin A, B, C, D, E, and the like, where cyclophilin A is of particular interest.

Instead of being an intracellular protein, the endogenous biodistribution modulating protein may be an extracellular or serum protein, e.g. where it is desired to target the bifunctional molecule to the extracellular space of the host to which the molecule is administered. Serum biodistribution modulating proteins of particular interest are those that are relatively abundant in the serum of the host and meet the above criteria for suitable endogenous biodistribution modulating proteins. By relatively abundant is meant that the concentration of the serum biodistribution modulating protein is at least about 1 ng/ml. usually at least about 10 μg/ml and more usually at least about 15 μg/ml. Specific serum proteins of interest as biodistribution modulating proteins include: albumin, Vitamin A binding proteins and Vitamin D binding proteins, β-2 macroglobulin, with albumin being a particularly preferred biodistribution modulating protein.

In yet other embodiments, targeting a certain cell or tissue type is of interest. In such embodiments, the targeting moiety is a moiety that binds to a biodistribution modulating protein that is substantially present only those cells or tissues that are to be targeted. For example, where one wishes to target melanoma cells, a protein that is present in the melanoma cells to a much greater extent than other types of cells in the host is melanin. As such, melanin may serve as a biodistribution modulating agent for a bifunctional molecule targeted to melanoma cells with a melanin binding agent, e.g. chloroquine, serving as the targeting moiety of the bifunctional molecule. Likewise, for targeting liver, quinacrine may be used as the targeting moiety. Similarly, for targeting microbes, FK506 homologues that bind to the FKBP homologs in the microbes may be employed as the targeting moiety. As such, the nature of the biodistribution modulating protein may vary greatly depending on the particular cell or tissue type to which targeting is desired.

In yet other embodiments, the bifunctional molecule is targeted to a subcellular location. For example, where one wishes to target a molecule to a membrane, diltiazem may be employed as the targeting moiety. In many such embodiments, a the targeting moiety will bind to a biodistribution modulating protein present in the subcellular location of interest.

The Z moiety of the subject bifunctional molecules will therefore be chosen in view of the endogenous biodistribution modulating protein that is to be used to home the drug moiety of the bifunctional molecule to the desired target. As such, the Z moiety may be a number of different ligands depending on the particular endogenous biodistribution modulating protein to which it is intended to bind, where certain exemplary ligands have been mentioned supra. In many preferred embodiments, the Z moiety has an affinity for its biodistribution modulating protein of at least about $10^{-4}$ M, usually at least about $10^{-6}$ molar and more usually at least about $10^{-8}$ M, where in many embodiments the Z moiety has an affinity for its biodistribution modulating protein of between about $10^{-9}$ and $10^{-12}$ M. The Z moiety portion of the bifunctional molecule should also be specific for the biodistribution modulating protein in the context of its binding activity when present in the bifunctional molecule, in that it does not significantly bind or substantially affect non-biodistribution modulating proteins when it is present in the bifunctional molecule.

Representative ligands capable of serving as the Z moiety of the bifunctional molecule include ligands for intracellular proteins such as: peptidyl-prolyl isomerase ligands, e.g. FK506, rapamycin, cyclosporin A and the like: Hsp90 ligands, e.g. geldanamycin: steroid hormone receptor ligands. e.g. naturally occurring steroid hormones, such as estrogen, progestin, testosterone, and the like, as well as synthetic derivatives and mimetics thereof, particularly those which bind with high specificity and affinity but do not activate their respective receptors; small molecules that bind to cytoskeletal proteins, e.g. antimitotic agents, such as taxanes, colchicine, colcemid, nocadozole, vinblastine, and vincristine, actin binding agents, such as cytochalasin, latrunculin, phalloidin, and the like.

As mentioned above, in certain preferred embodiments the intracellular biodistribution modulating proteins are members of the peptidyl-prolyl isomerase family, particularly the FKBP and cyclophilin subsets of this family. Where peptidyl-prolyl isomerase biodistribution modulating proteins are employed, the bifunctional molecule/peptidyl-prolyl isomerase complex will preferably not substantially bind to the natural peptidyl-prolyl isomerase/ligand target calcineurin so as to result in significant immunosuppression. A variety of ligands are known that bind to FKBPs and may be used in the subject invention. The ligands should specifically bind to an FKBP and have an affinity for the FKBP that is between about $10^{-6}$ and $10^{-10}$ M. Of interest are both naturally occurring FKBP ligands, including FK506 and rapamycin. Also of interest are synthetic FKBP ligands, including those described in U.S. Pat. Nos. 5,665,774; 5,622,970; 5,516,797; 5,614,547, and 5,403,833. the disclosures of which are herein incorporated by reference.

Also of interest in this particular set of preferred embodiments are cyclophilin ligands where such ligands should specifically bind to cyclophilin with an affinity that is between about $10^{-6}$ and $10^{-9}$. A variety of ligands that bind to cyclophilins are also known, where such ligands include the naturally occurring cyclosporins, such as cyclosporin A, as well as synthetic derivatives and mimetics thereof, including those described in U.S. Pat. Nos. 5,401,649; 5,318,901; 5,236,899; 5,227,467; 5,214.130; 5,122,511; 5,116,816; 5,089,390; 5,079,341; 5,017,597; 4,940,719; 4,914,188; 4,885,276; 4,798,823; 4,771,122; 4,703,033; 4,554,351; 4,396,542: 4,289,851; 4,288,431; 4,220,610 and 4,210,581, the disclosures of which are herein incorporated by reference.

Representative ligands for use as the Z moiety in the bifunctional molecule also include ligands that bind to extracellular biodistribution modulating proteins. Such ligands should specifically bind to their respective biodistribution modulating protein with an affinity of at least about $10^{-4}$ M. Ligands of interest for use in binding to extracellular biodistribution modulating proteins include: albumin ligands, such as arachidonate, bilirubin, hemin, aspirin, ibuprofen, para-amino salicylic acid, myristylate, plamitate, linoleate, warfarin, sulfisoxazole, etc.: Vitamin A and derivatives thereof, Vitamin D and derivatives thereof, and the like.

Representative ligands for use as the Z moiety in the bifunctional molecule also include ligands that target the molecule to a specific cell or tissue type, e.g. melanin binding moieties, e.g. chloroquine, for targeting melanoma cells, quinacrine for targeting liver cells, and the like.

Linking Moiety: L

The Z and X moieties of the bifunctional molecule are joined together through linking moiety L, where L may be either a bond or a linking group. Where linking groups are employed, such groups are chosen to provide for covalent attachment of the drug and ligand moieties through the linking group, as well as the desired structural relationship of the bifunctional molecule with respect to its intended biodistribution modulating protein. Linking groups of interest may vary widely depending on the nature of the drug and ligand moieties. The linking group, when present, should preferably be biologically inert. Appropriate linkers can readily be identified using the affinity, specificity or selectivity assays described supra. A variety of linking groups are known to those of skill in the art and find use in the subject bifunctional molecules. The linker groups should be sufficiently small so as to provide a bifunctional molecule having the overall size characteristics as described above, the size of the linker group, when present, is generally at least about 50 daltons, usually at least about 100 daltons and may be as large as 1000 daltons or larger, but generally will not exceed about 500 daltons and usually will not exceed about 300 daltons. Generally, such linkers will comprise a spacer group terminated at either end with a reactive functionality capable of covalently bonding to the drug or ligand moieties. Spacer groups of interest include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid). 4,4'-ethylenedipiperidine. Potential reactive functionalities include nucleophilic functional groups (amines, alcohols, thiols, hydrazides) electrophilic functional groups (aldehydes esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linker groups that may find use in the subject bifunctional molecules include heterofunctional compounds, such as azidobenzoyl hydrazide, N-[4-(p-azidosalicylamino) butyl]-3'-[2'-pyridyldithio]propionamid), bis-sulfosuccinimidyl suberate, dimethyladipimidate, disuccinimidyltartrate, N—-maleimidobutyryloxysuccinimide ester, N-hydroxy sulfosuccinimidyl-4-azidobenzoate, N-succinimidyl[4-azidophenyl]-1,3'-dithiopropionate, N-succinimidyl[4-iodoacetyl]aminobenzoate, glutaraldehyde, and succinimidyl 4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like.

Methods of Making Targeted Bifunctional Molecules

The bifunctional molecules of the subject invention may be prepared using any convenient methodology. In many embodiments of the subject invention, the invention is used to modulate the biodistribution of an identified and at least partially characterized small molecule drug. Generally, a small molecule drug of interest is first identified. The drug may be a previously identified biologically active agent or compound having the desired target binding activity, or one that has been newly discovered using one or more drug discovery techniques. The bifunctional molecule is then generally produced from the to drug using a rational or combinatorial approach.

In a rational approach, the bifunctional molecules are constructed from their individual components, e.g. targeting moiety, linker and drug. The components can be covalently bonded to one another through functional groups, as is known in the art, where such functional groups may be present on the components or introduced onto the components using one or more steps, e.g. oxidation reactions, reduction reactions, cleavage reactions and the like. Functional groups that may be used in covalently bonding the components together to produce the bifunctional molecule include: hydroxy, sulfhydryl, amino, and the like. The particular portion of the different components that are modified to provide for covalent linkage will be chosen so as not to substantially adversely interfere with that components desired binding activity, e.g. for the drug moiety, a region that does not affect the target binding activity will be modified such that a sufficient amount of the desired drug activity is preserved. Where necessary and/or desired, certain moieties on the components may be protected using blocking groups, as is known in the art, see, e.g. Green & Wuts, Protective Groups in Organic Synthesis (John Wiley & Sons) (1991).

The above component approach to production of the bifunctional molecule is best suited for situations where the three-dimensional structures of the biodistribution modulating protein, the targeting moiety, the drug and the target are known such that molecular modeling can be used to determine the optimal linker size, if any, to be employed to join the different components.

Alternatively, the bifunctional molecule can be produced using combinatorial methods to produce large libraries of potential bifunctional molecules which may then be screened for identification of a bifunctional molecule with the biodistribution profile. Methods for producing and screening combinatorial libraries of molecules include: 5,741,713; 5,734, 018; 5,731,423; 5,721,099; 5,708,153; 5,698,673; 5,688,997; 5,688,696; 5,684,711; 5,641,862; 5,639.603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Alternatively, the bifunctional molecule may be produced using medicinal chemistry and known structure-activity relationships for the targeting moiety and the drug. In particular, this approach will provide insight as to where to join the two moieties to the linker.

Screening Bifunctional Compounds

The resultant bifunctional molecules are then screened for those molecules that exhibit the desired biodistribution profile. Any convenient screening assay may be employed, where the particular screening assay may be one known to those of skill in the art or one developed in view of the specific molecule and property being studied. Typically, the screening assay will involve observing the biodistribution of the bifunctional molecule and comparing it to a free drug control, e.g. a suitable animal model. As such, one can administer labeled bifunctional molecule, e.g. isotopically labeled bifunctional molecule, to a test animal and then observe its biodistribution in the animal at one or more time periods following administration of the bifunctional compound. By comparing the observed results to those obtained with a control, the biodistribution of the bifunctional compound can be evaluated with respect to whether it is modulated as compared to a free drug control. Other assays for identifying those bifunctional molecules that exhibit at least a modulated biodistribution as compared to a free drug control may be employed, as desired.

Methods for Making Targeted Bifunctional Molecules for Peptidyl-Prolyl Isomerase Biodistribution Modulating Proteins As mentioned above, one class of preferred embodiments of the subject invention are those embodiments in which the bifunctional molecules are specifically targeted to the intracellular space of a host. In these embodiments, of particular interest are those bifunctional molecules in which the targeting moiety specifically binds to endogenous peptidyl-prolyl isomerase biodistribution modulating proteins present in the host into which the bifunctional molecule is introduced. Thus, bifunctional molecules of interest include those in which the endogenous biodistribution modulating protein is either an FKBP or a cyclophilin.

In preparing bifunctional molecules from FK506, a suitable attachment site on the FK506 structure is identified, modified as necessary, and then covalently attached to the linker or drug moiety. The structure of FK506 (also known as tacrolimus) is:

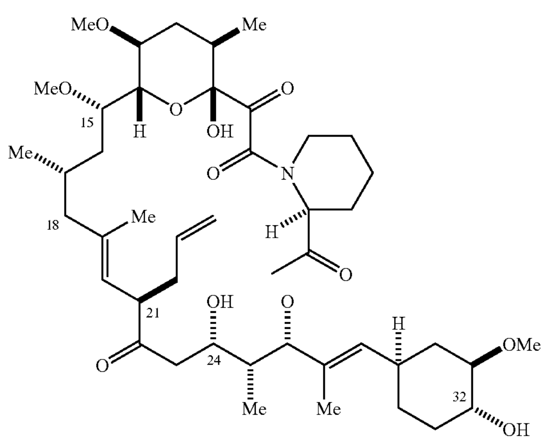

The site to which the linker/drug moiety is covalently attached is one that, upon covalent attachment, does not ablate the affinity and/or specificity of FK506 for its FKBP biodistribution modulating protein, e.g. FKBP 12 or FKBP 52. As such, positions suitable for use as covalent linkage sites include atoms located between carbon 15 and carbon 25 and the substituents attached to these atoms. For example, oxidation of the allyl group or oxidation of the carbon 18 methylene group: modification of the carbon 22 ketone or the carbon 24 hydroxyl group or alkylation at carbon 21 or carbon 23; as well as the secondary hydroxyl group located on the cyclohexyl ring (carbon 32); are potential specific covalent linkage sites.

With FK506, depending on the drug moiety and/or linker to be attached, it may be desirable to introduce one or more functional moieties onto the FK506 structure. Functional moieties of interest that may be introduced include: hydroxyl groups, amino groups, carboxyl groups, aldehydes, carbonates, carbamates, azides, thiols, and esters, etc. Such groups may be introduced using known protocols, such as oxidation reactions, reduction reactions, cleavage reactions and the like, with or without the use of one or more blocking groups to prevent unwanted side reactions.

In some instances, it is desirable to covalently attach the drug moiety directly to FK506, often activated FK506. In such instances, the reactive functional group(s) introduced onto the FK506 structure will depend primarily on the nature of the drug moiety to be attached. Thus, for peptidic drug moieties, specific pairings of interest include: FK506 carbonates for reacting with amino groups of peptides: FK506 carboxylic acids for reacting with amino groups of peptides; FK506 amines for reacting with carboxylic acid groups of peptides; FK506 maleimide for reacting with thiol groups of peptides; and the like. Alternatively, where the drug moiety is a steroid, potential pairings of interest include: FK506 N-hydroxysuccinimidyl carbonate and partner amine; FK506 aldehyde and partner amine; FK506 aldehyde and partner hydrazide; FK506 hydroxy group and partner carboxylic acid OR alkyl halide: FK506 thiol and partner maleimide and the like.

Following introduction of the reactive functional group(s) onto the FK506 structure, the activated FK506 is then combined with the drug moiety/linker under conditions sufficient for covalent bonding to occur.

Another embodiment of particular interest are bifunctional molecules of cyclosporin A or analogs thereof. The structure of cyclosporin A is:

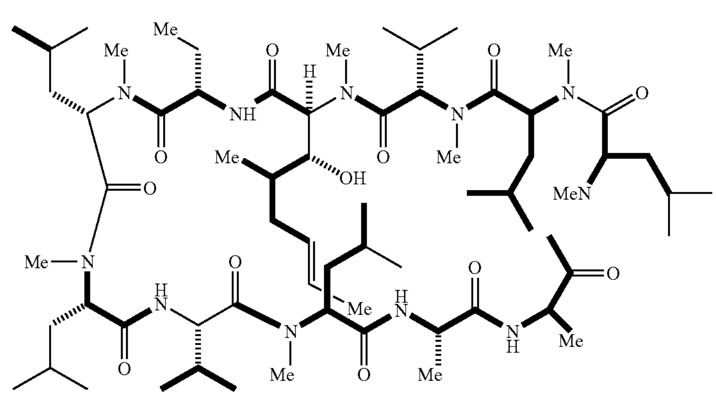

As with the FK506 bifunctional molecules, the cyclosporin A will be conjugated to the drug moiety in a manner such that cyclosporin A does not substantially lose its affinity for cyclophilin. Preferred positions on the cyclosporin A structure that may serve as covalent linkage sites include: residues 4, 5, 6, 7, 8: while less preferred but still possible residues include: 1, 2, 3, 9, 10 and 11. Where necessary, reactive functionalities may be introduced onto the cyclosporin structure, where such functionalities include: hydroxyl groups, amino groups, carboxyl groups, aldehydes, carbonates, carbamates, azides, thiols, and esters, etc., with the particular functionality of interest being chosen with respect to the specific linker or drug moiety to be attached.

Specific Improvements as Compared to Free Drug

As mentioned above, the bifunctional molecules of the subject invention exhibit modulated biodistribution upon administration of to a host as compared to their corresponding free drug, i.e. a free drug control. In other words, the biodistribution of the subject targeted bifunctional compounds differs from that of the corresponding free drug. In many embodiments, this modulated biodistribution results in at least one of enhanced efficacy and reduced toxicity. Enhanced efficacy can be evaluated by determining the amount of drug that is needed to cause a desired pharmacologic effect, where of interest are those bifunctional compounds that exhibit at least a 2 fold, usually at least a 4 fold and more usually at least a 10 greater activity than their corresponding free drug control. Toxicity may be evaluated by determining the presence and severity of side effects following administration of the bifunctional molecule where a reduction in toxicity of at least about 2 fold usually at least about 4 fold and more usually at least about 10 fold as compared to the corresponding free drug control is of interest.

The above improvements are achieved by selecting the appropriate target moiety which results in a modification of the distribution profile of the drug so that it is present in an enhanced amount in the desired host compartment, e.g. extracellular space, intracellular space, cell or tissue type, subcellular location, etc., as compared to undesired host compartments. By enhanced amount is meant an amount that is at least 30%, usually at least 100% and more usually at least 300% more.

In certain embodiments, the above improvements are achieved through the formation of binary or tripartite complexes as described in application Ser. No. 09/316,932 entitled Bifunctional Molecules and Therapies Based Thereon (where the presenter protein described therein is analogous to the biodistribution modulating protein described herein) the disclosure of which is herein incorporated by reference.

Methods of Use, Pharmaceutical Preparations and Kits

The subject bifunctional molecules find use in the pharmacological treatment of a host condition, e.g. a disease condition. In the methods of the subject invention, an effective amount of the bifunctional molecule is administered to the host where "effective amount" means a dosage sufficient to produce the desired result, e.g. an improvement in a disease condition or the symptoms associated therewith. In many embodiments, the amount of drug in the form of the bifunctional molecule that need be administered to the host in order to be an effective amount will vary from that which must be administered in free drug form where by free drug is meant drug that is not conjugated with another moiety, e.g. as is found in the subject bifunctional molecules. In certain embodiments, e.g. where the resultant modulated distribution results in enhanced activity as compared to the free drug control, the amount of drug that need be administered to be an effective amount is less than the amount of corresponding free drug that needs to be administered, where the amount may be 2-fold, usually about 4-fold and more usually about 10-fold less than the amount of free drug that is administered. In certain other embodiments, e.g. where the bifunctional molecule exhibits reduced toxicity as compared to the free drug, a larger amount of bifunctional molecule may be administered as compared to the free drug where the increased amount may be increased by about 2-fold, usually at least about 4-fold and more usually at least about 10-fold.

The bifunctional molecule may be administered to the host using any convenient means capable of producing the desired result. Thus, the bifunctional molecule can be incorporated into a variety of formulations for therapeutic administration. More particularly, the bifunctional molecule of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the bifunctional molecule can be achieved in various ways, including oral, buccal, rectal, parenteral, intraperitoneal, intradermal, transdermal, intracheal, etc. administration. In pharmaceutical dosage forms, the bifunctional molecule may be administered alone or in combination with other pharmaceutically active compounds. The following methods and excipients are merely exemplary and are in no way limiting.

For oral preparations, the bifunctional molecules can be used alone or in combination with appropriate additives to make tablets, powders, granules or capsules, for example, with conventional additives, such as lactose, mannitol, corn starch or potato starch: with binders, such as crystalline cellulose, cellulose derivatives, acacia, corn starch or gelatins; with disintegrators, such as corn starch, potato starch or sodium carboxymethylcellulose: with lubricants, such as talc or magnesium stearate: and if desired, with diluents, buffering agents, moistening agents, preservatives and flavoring agents.

The bifunctional molecules can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol: and if desired, with conventional additives such as solubilizers, isotonic agents, suspending agents, emulsifying agents, stabilizers and preservatives.

The bifunctional molecules can be utilized in aerosol formulation to be administered via inhalation. The compounds of the present invention can be formulated into pressurized acceptable propellants such as dichlorodifluoromethane, propane, nitrogen and the like.

Furthermore, the bifunctional molecules can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols which melt at body temperature yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing active agent. Similarly, unit dosage forms for injection or intravenous administration may comprise the active agent in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host. The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

The subject methods find use in the treatment of a variety of different disease conditions. In certain embodiments, of particular interest is the use of the subject methods in disease conditions where an active agent or drug having desired activity has been previously identified, but which active agent or drug does not bind to its target with desired affinity and/or specificity. With such active agents or drugs, the subject methods can be used to enhance the binding affinity and/or specificity of the agent for its target. The specific disease conditions treatable by with the subject bifunctional compounds are as varied as the types of drug moieties that can be present in the bifunctional molecule. Thus, disease conditions include cellular proliferative diseases, such as neoplastic diseases, autoimmune diseases, cardiovascular diseases, hormonal abnormality diseases, infectious diseases, and the like.

By treatment is meant at least an amelioration of the symptoms associated with the disease condition afflicting the host, where amelioration is used in a broad sense to refer to at least a reduction in the magnitude of a parameter, e.g. symptom, associated with the pathological condition being treated, such as inflammation and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the bifunctional molecule, usually in oral or injectable doses and often in a storage stable formulation, are provided. In such kits, in addition to the containers containing the unit doses will be an informational package insert describing the use and attendant benefits of the drugs in treating pathological condition of interest. Preferred compounds and unit doses are those described herein above.

The following examples are offered by way of illustration and not by way of limitation.

EXPERIMENTAL

I. Targeting to the Extracellular Space

A bifunctional molecule is designed which is targeted to the extracellular space. The bifunctional molecule consists of a drug moiety covalently joined to sulfisoxazole (a non-toxic molecule that is extensively bound by albumin) via an inert linking group. When this bifunctional molecule enters the human circulation, it is bound by albumin which keeps the drug of interest in the extracelluar environment.

II Targeting to the Intracellular Space

Bifunctional molecules having a drug of interest covalently bound through an inert linking group to either FK506 or rapamycin, or their derivatives that display a high affinity for FKBP, are prepared. See e.g. U.S. patent application Ser. No. 09/316,932, the disclosure of which is herein incorporated by reference. By linking these molecules to a drug of interest, one can target them to and retain them inside of cells. Since the FKBP pool in all cells is very large, a drug of interest is also greatly accumulated intracelluarly. Other targeting proteins may not be expressed at high concentrations or may have ligands with only intermediate affinity. In those cases the accumulation effect will be smaller than with FKBP ligands.

III. Targeting Melanoma Cells

Of great importance is the approach to target drugs of interest to specific cells and tissues. Antiproliferative drugs like doxorubicin, methotrexate, vincristine, etoposide, piritrexim, mitomycin or bleomycin effect not only cancerous cells but all other dividing cells as well. In order to target such drugs to neoplastic cells, a bifunctional molecule is prepared that contains a ligand that binds to a protein which is expressed preferentially in the target cells. For example, chloroquine is a molecule that has a high affinity for melanin which is expressed in melanocytes. Piritrexim is a dihydrofolate reductase (DHFR) inhibitor which has shown good activity against melanoma. Hence, chloroquine may be used to target piritrexim to melanoma cells which would enhance the activity of piritrexim against melanoma and would reduce the overall concentration of piritrexim required to treat the disease.

IV. Targeting Liver Cells

Quinacrine, like chloroquine, is an anti-malarial drug. Quinacrine accumulates in the liver and could therefore be used to target drugs to hepatoma cells. As such, a bifunctional molecule is prepared that includes a drug of interest covalently joined to quinacrine by an inert linking group.

V. Targeting Microbial Cells

Anti-infectives like novobiocin, trimetrexate or rifampicin often cause side effects because they target the same metabolic pathways or enzymatic activities in humans and microbes. In order to target an antimicrobial agent of interest to microbial cells, a bifunctional molecule in which the antimicrobial is linked to a molecule that binds a protein which is specifically expressed in the pathogen is prepared. For example, many microbes express FKBP homologues that do not bind FK506 with high affinity because of amino acid substitutions in the FK506 binding pocket. One can chemically introduce compensatory changes in FK506 so that the resulting FK506 derivatives will bind the microbial FKBPs with high affinity but will not bind the human FKBP any more. Bifunctional molecules containing the new FK506 derivatives and the drug of interest are therefore prepared which target drugs of interest to microbial cells.

VI. Targeting to a Subcellular Location

Selective targeting is also useful with respect to the desired subcellular localization of the drug of interest. Bifunctional molecules are prepared that target a drug moiety to compartments in a cell like the nucleus, mitochondria, the endoplasmic reticulum and the plasma membrane, nuclear membrane or other membranes. For example, diltiazem is a molecule that imbeds itself in the plasma membrane. Bifunctional molecules that use diltiazem as the targeting moiety bring a drug moiety to the immediate proximity of the plasma membrane which is the location of many drug targets like receptors, ion channels or adhesion molecules.

It is evident from the above results and discussion that the subject invention provides a powerful tool for improving drug safety and/or efficacy of a drug by targeting small molecule drugs to desired biological compartments and therefore modulating the biodistribution of the drugs. As such, the subject method provides for the improvement of drugs currently in use, e.g. by increasing efficacy and/or or reducing unwanted side effects. Furthermore, the subject methods can be used to improve drugs that have, until now, been clinically useless due to considerable toxicity in humans and animals. Therefore, the invention provides for the potential usefulness of the variety of previously discovered and discarded biologically active compounds. Accordingly, the invention provides an important advancement in pharmacological science.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for directing the biodistribution of a drug that binds to a protein target, wherein the drug is directed to an intracellular space upon administration to a mammalian host, said method comprising:

administering to said mammalian host an effective amount of a bifunctional molecule having a molecular weight that does not exceed about 5000 daltons consisting of a drug moiety comprising said drug or an active derivative thereof and a targeting moiety to an intracellular biodistribution modulating protein optionally joined by a linking group, wherein said drug moiety binds to a naturally occurring protein target and said targeting moiety is a peptidyl-prolyl isomerase ligand, and wherein said bifunctional molecule has a modulated biodistribution upon administration to said mammalian host as compared to a free drug control;

to direct said biodistribution of said drug upon administration to said host to an intracellular space as compared to a free drug control.

2. The method according to claim 1, wherein said bifunctional molecule exhibits enhanced efficacy upon administration to said mammalian host as compared to a free drug control.

3. The method according to claim 1, wherein said bifunctional molecule exhibits reduced toxicity upon administration to said mammalian host as compared to a free drug control.

4. The method according to claim 1, wherein said bifunctional molecule comprises a linking group.

5. The method according to claim 1, wherein said bifunctional molecule is administered as a pharmaceutical preparation.

6. A method for targeting a drug to an intracellular site of a mammalian host, said method comprising:

administering to said mammalian host an effective amount of a bifunctional molecule having a molecular weight that does not exceed about 5000 daltons consisting of a drug moiety and a targeting moiety optionally joined by a linking group, wherein said drug moiety and targeting moiety bind to naturally occurring intracellular proteins and said targeting moiety is a peptidyl-prolyl isomerase ligand, and wherein said bifunctional molecule exhibits a modulated biodistribution upon administration to a mammalian host as compared to a free drug control;

to target said drug to an intracellular site of a mammalian host.

7. The method according to claim 6, wherein said bifunctional molecule comprises a linking group.

8. The method according to claim 6, wherein said bifunctional molecule does not include a linking group.

9. The method according to claim 1, wherein said peptidyl-prolyl isomerase ligand is a ligand for an FKBP or cyclophilin.

10. The method according to claim 1, wherein said peptidyl-prolyl isomerase ligand is a ligand for an FKBP.

11. The method according to claim 10, wherein said ligand for an FKBP is selected from the group consisting of FK506 and rapamycin.

12. The method according to claim 1, wherein said peptidyl-prolyl isomerase ligand is a ligand for a cyclophilin.

13. The method according to claim 12, wherein said ligand for a cyclophilin is a cyclosporin.

14. The method according to claim 6, wherein said peptidyl-prolyl isomerase ligand is a ligand for an FKBP or cyclophilin.

15. The method according to claim 6, wherein said peptidyl-prolyl isomerase ligand is a ligand for an FKBP.

16. The method according to claim 15, wherein said ligand for an FKBP is selected from the group consisting of FK506 and rapamycin.

17. The method according to claim 6, wherein said peptidyl-prolyl isomerase ligand is a ligand for a cyclophilin.

18. The method according to claim 17, wherein said ligand for a cyclophilin is a cyclosporin.

19. A method for directing the biodistribution of a drug that binds to a protein target, wherein the drug is directed to an intracellular space upon administration to a mammalian host, said method comprising:

administering to said mammalian host an effective amount of a bifunctional molecule having a molecular weight that does not exceed about 5000 daltons consisting of a drug moiety comprising said drug or an active derivative thereof and a peptidyl-prolyl isomerase ligand optionally joined by a linking group, wherein said bifunctional molecule has a modulated biodistribution upon administration to said mammalian host as compared to a free drug control and binds to an endogenous peptidyl-prolyl isomerase to produce a bifunctional molecule/endogenous peptidyl-prolyl isomerase complex that does not bind to calcineurin;

to direct said biodistribution of said drug upon administration to said host to an intracellular space as compared to a free drug control.

20. The method according to claim 19, wherein said bifunctional molecule exhibits enhanced efficacy upon administration to said mammalian host as compared to a free drug control.

21. The method according to claim 19, wherein said bifunctional molecule exhibits reduced toxicity upon administration to said mammalian host as compared to a free drug control.

22. The method according to claim 19, wherein said bifunctional molecule comprises a linking group.

23. The method according to claim 19, wherein said bifunctional molecule is administered as a pharmaceutical preparation.

24. The method according to claim 19, wherein said mammalian host is human.

25. The method according to claim 19, wherein said drug is a small molecule.

26. The method according to claim 19, wherein said peptidyl-prolyl isomerase ligand is a ligand for an FKBP or cyclophilin.

27. The method according to claim 19, wherein said peptidyl-prolyl isomerase ligand is a ligand for an FKBP.

28. The method according to claim 19, wherein said peptidyl-prolyl isomerase ligand is a ligand for a cyclophilin.

29. The method according to claim 1, wherein said administering results in the formation of an intracellular tripartite complex comprising said naturally occurring protein target, said naturally occurring peptidyl-prolyl isomerase and said bifunctional molecule, and wherein the formation of said intracellular tripartite complex results in said modulated biodistribution of said bifunctional molecule.

* * * * *